(12) United States Patent
Sim et al.

(10) Patent No.: US 9,795,546 B2
(45) Date of Patent: Oct. 24, 2017

(54) COMPOSITION FOR BLEACHING TOOTH

(71) Applicant: DENT-WHITE CO., LTD., Paju (KR)

(72) Inventors: Jae Hyun Sim, Paju (KR); Bong Kyu Choi, Seoul (KR)

(73) Assignee: DENT-WHITE CO., LTD., Paju-si (KR)

( * ) Notice: Subject to any disclaimer, the term of this patent is extended or adjusted under 35 U.S.C. 154(b) by 0 days.

(21) Appl. No.: 15/024,886

(22) PCT Filed: Sep. 25, 2014

(86) PCT No.: PCT/KR2014/008975
§ 371 (c)(1),
(2) Date: Mar. 25, 2016

(87) PCT Pub. No.: WO2015/046922
PCT Pub. Date: Apr. 2, 2015

(65) Prior Publication Data
US 2016/0220460 A1 Aug. 4, 2016

(30) Foreign Application Priority Data
Sep. 27, 2013 (KR) .................. 10-2013-0115257

(51) Int. Cl.
*A61Q 11/00* (2006.01)
*A61K 8/22* (2006.01)
*A61K 8/29* (2006.01)
*A61K 8/02* (2006.01)

(52) U.S. Cl.
CPC .............. *A61K 8/29* (2013.01); *A61K 8/0216* (2013.01); *A61K 8/0241* (2013.01); *A61K 8/22* (2013.01); *A61Q 11/00* (2013.01); *A61K 2800/412* (2013.01); *A61K 2800/413* (2013.01)

(58) Field of Classification Search
CPC ...... A61Q 11/00; A61K 8/22; A61K 2800/92; A61K 8/29
See application file for complete search history.

(56) References Cited

U.S. PATENT DOCUMENTS

| | | | | |
|---|---|---|---|---|
| 4,910,014 A | * | 3/1990 | Nakagawa | A61K 8/29 424/49 |
| 6,843,981 B1 | * | 1/2005 | Ishibashi | A61K 8/22 424/53 |

FOREIGN PATENT DOCUMENTS

| | | |
|---|---|---|
| JP | 2004-292429 | 10/2004 |
| JP | 2007-161623 | 6/2007 |
| KR | 10-2002-0033650 | 5/2002 |
| KR | 10-2003-0076632 | 9/2003 |

OTHER PUBLICATIONS

Search Report & Written Opinion, Patent Cooperation Treaty, Application No. PCT/KR2014/008975, dated Jan. 14, 2015.
Jing Sun et al., "Synthesizing and Comparing the Photocatalytic Properties of High Surface Area Rutile and Anatase Titania Nanoparticles", J. Am. Ceram. Soc., 86 [10], pp. 1677-1682, Oct. 2003.
Kan Fujihara et al., "Time-resolved photoluminescence of particulate TiO2 photocatalysts suspended in aqueous solutions", Journal of Photochemistry and Photobiology A: Chemistry 132, pp. 99-104, Mar. 20, 2000.

* cited by examiner

*Primary Examiner* — Tracy Liu
(74) *Attorney, Agent, or Firm* — Lex IP Meister, PLLC

(57) ABSTRACT

Provided is a composition for bleaching tooth. The composition for bleaching tooth of the present invention includes rutile type titanium dioxide, peroxide, and water. The composition for bleaching tooth of the present invention exhibits a superior bleaching effect, compared to commercially available bleaching compositions.

4 Claims, 1 Drawing Sheet

[FIG. 1]
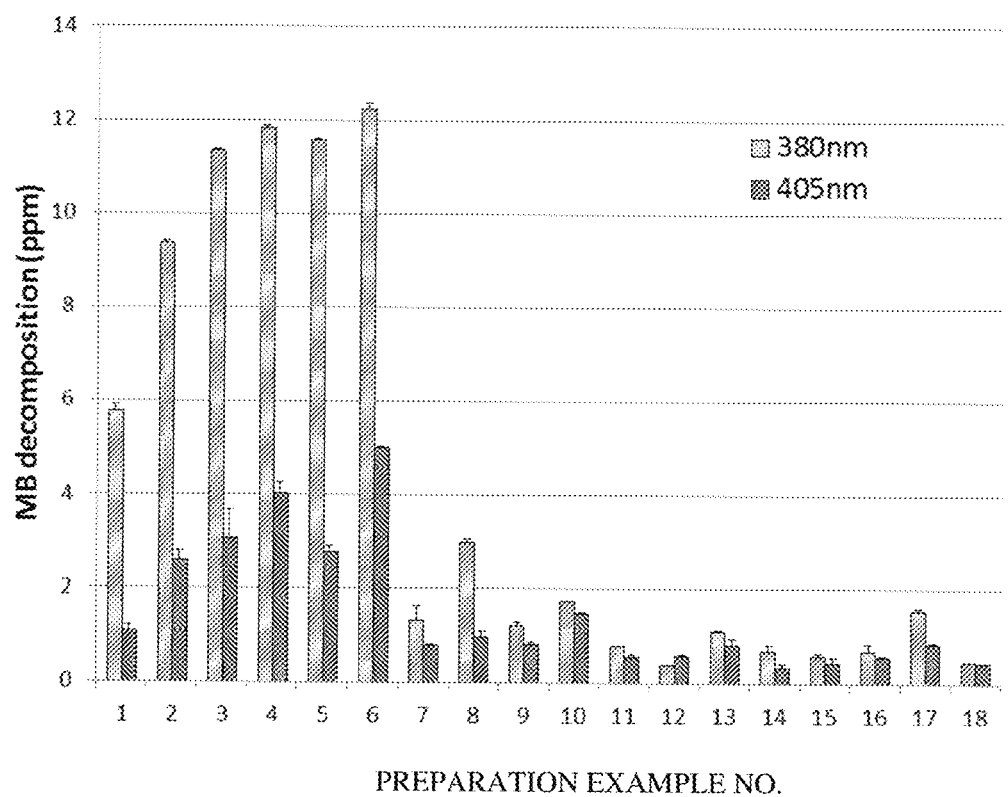
PREPARATION EXAMPLE NO.
[FIG. 2]
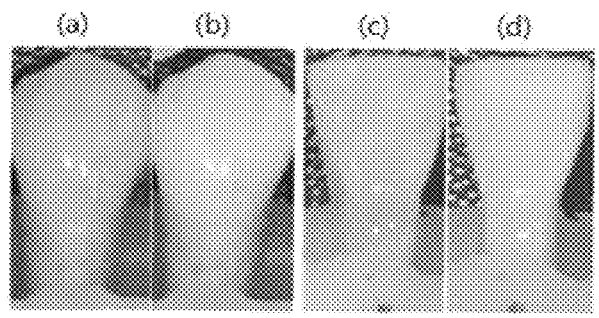

US 9,795,546 B2

COMPOSITION FOR BLEACHING TOOTH

BACKGROUND OF THE INVENTION (a) Field of the Invention

The present disclosure relates to a composition for bleaching tooth, and more particularly, to a composition for bleaching tooth showing an excellent bleaching effect.

The present application is based on, and claims priority from Korean Patent Application No. 10-2013-0115257, filed on Sep. 27, 2013, the disclosure of which is hereby incorporated by reference herein in its entirety.

(b) Description of the Related Art

Tooth discoloration that has been known until now may be divided into intrinsic tooth discoloration caused by nerve injury inside tooth, aging, or overuse of antibiotics such as tetracycline, and extrinsic tooth discoloration caused by food or tobacco debris, coffee, black tea, etc. deposited on the outer surface of tooth.

Tooth bleaching which is performed to improve tooth discoloration includes a home bleaching method self-administered and an office bleaching method professionally administered. Compared to the home bleaching, the office bleaching uses a tooth bleaching agent containing a relatively high concentration of hydrogen peroxide and also an activation system such as heat and light in order to enhance the tooth bleaching effect. Since there is a concern about damage of the tooth nerve due to the system using heat, a system of enhancing the tooth bleaching effect by using light has been preferred.

Although the light-activated system is preferred, there are few light activators of which light catalytic activity has been proven. Further, the tooth bleaching effect of the light-activated system is still under controversy. Some studies reported that the light-activated system produced much better bleaching effects than a non-light system. However, another study reported that there was no difference between the light-activated system and the non-light system. Likewise, superiority of the light-activated system over the non-light system has not been clearly demonstrated yet.

The light activator used in the tooth bleaching agent is required to have high chemical stability as well as its light catalytic activity. The tooth bleaching agent contains a high concentration of hydrogen peroxide as a strong peroxide. Therefore, if the light activator is not chemically stable, it is oxidized before acting as a catalyst. Hydrogen peroxide is known as a material having an oxidative power strong enough to decompose a variety of industrial organic or inorganic pollutant. Compounds having hydroxyl or ketone groups may be easily decomposed or oxidized in the presence of hydrogen peroxide. Therefore, organic compounds or complexes containing organic compounds are not suitable as light catalysts of tooth bleaching agents.

SUMMARY OF THE INVENTION

In order to solve the above problems of the prior art, an object of the present invention is to provide a composition for bleaching tooth, which is used to obtain an excellent bleaching effect.

In order to achieve the above object, the present invention provides a composition for bleaching tooth including rutile type titanium dioxide having an average particle size of 30 to 180 nm, peroxide, and water.

In the composition for bleaching tooth according to the present invention, rutile type titanium dioxide having an average particle size of 30 to 180 nm functions as a light activator, thereby providing an excellent bleaching effect.

BRIEF DESCRIPTION OF THE DRAWINGS

FIG. 1 is a graph showing a comparison of methylene blue decomposition by titanium dioxide solutions of Preparation Examples 1 to 18 and a hydrogen peroxide aqueous solution; and FIG. 2 shows images of comparing bleaching effects before and after application of compositions for bleaching tooth of Example 3 and Comparative Example 13.

DETAILED DESCRIPTION OF THE EMBODIMENTS

The terms first, second, etc. may be used herein to describe various elements, and these terms are used only for distinguishing one component from the other component.

Further, terminologies used herein are for the purpose of explaining exemplary embodiments and have no intention to limit the present invention. Unless the context indicates otherwise, a singular expression may include a plural expression. It will be understood that the term "comprise", "include", or "have" used herein is intended to refer to the presence of stated features, integers, steps, components, or combinations thereof, but not to preclude the existence or addition of one or more other features, integers, steps, components or combinations thereof.

Further, in the present invention, when a layer or an element is referred to as being "on" or "over" layers or elements, it can be directly on the layers or elements, or the other layers or elements can be additionally formed between the layers, or on an object or a substrate.

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, a composition for bleaching tooth of the present invention will be described in more detail.

The composition for bleaching tooth of the present invention includes rutile type titanium dioxide ($TiO_2$) having an average particle size of 30 to 180 nm, peroxide, and water.

Titanium dioxide ($TiO_2$) is one of the most widely used inorganic photocatalysts in the world, because of its physical and chemical stability, high catalytic activity, low cost, and non-toxicity. The mechanism of photoactivity of titanium dioxide is relatively well established, and titanium dioxide is known to be used as a tooth bleaching agent.

However, two problems must be solved in order to use titanium dioxide as a light activator.

First, titanium dioxide only exhibits effective photoactivity when irradiated by light in the ultraviolet range. Titanium dioxide has a relatively large energy band gap of 3.2 eV, and it may be activated in the wavelength range of 300 to 380 nm Although titanium dioxide is reported to be effective up to a wavelength of 380 nm, it actually exhibits a maximum absorbance near 340 nm. Since tooth bleaching agents are practically used at a wavelength of 380 to 420 nm, there is a need to extend the effective wavelength limit to the visible light wavelength of 380 to 420 nm Many methods have been tried to extend the effective wavelength range by reducing the energy band gap of titanium dioxide, and a representative method is doping. The energy band gap of titanium dioxide may be reduced by doping the surface with a metallic or non-metallic material, thereby extending the effective wavelength to the visible light wavelength. However, doping increases a hole-electron recombination rate, and therefore, photoactivity efficiency of titanium dioxide may be reduced in both the visible and ultraviolet ranges, compared to undoped titanium dioxide.

Further, titanium dioxide exhibits different photoactive results depending on its particle size, crystallinity, surface treatment, shape, etc. The previous studies reported that anatase crystalline titanium dioxide has a much higher photoactivity than rutile crystalline titanium dioxide, and for titanium dioxide of the same weight, titanium dioxide having a smaller particle size has a higher photoactivity because it has a larger surface area.

However, the present invention revealed that rutile type titanium dioxide exhibits a higher photoactivity than titanium dioxide having different crystallinity such as anatase type, or amorphous titanium dioxide, and thus, it exhibits superior tooth bleaching effect when applied to tooth bleaching by light irradiation. The present invention also revealed that titanium dioxide having a smaller particle size does not exhibit higher photoactivity, but there is an optimum particle size, which may exhibit a relatively high photoactivity.

According to an embodiment of the present invention, the composition for bleaching tooth of the present invention includes a rutile type titanium dioxide, in which the rutile type titanium dioxide has an average particle size of about 30 to about 180 nm, or about 50 to about 180 nm, or about 30 to about 165 nm, or about 50 to 165 nm or about 50 to 100 nm. If the average particle size of titanium dioxide is too small or too large out of the above range, photoactivity may be reduced, and in particular, titanium dioxide having an excessively small particle size may exhibit toxicity. Therefore, when the average particle size of titanium dioxide is within the above range, titanium dioxide may exhibit the most effective photoactivity without toxicity to human body. Further, the shape of rutile type titanium dioxide is not particularly limited, but spherical or nearly spherical titanium dioxide may be used.

Further, it is preferable that the rutile type titanium dioxide does not substantially include other impurity elements.

The phrase "does not substantially include other impurity elements" means that the rutile type titanium dioxide is used as it is without mixing the titanium dioxide with other elements or compounds by a method such as surface treatment, doping, coating, etc. Therefore, purity of the rutile type titanium dioxide is preferably about 97% or higher, or about 99% or higher, or about 99.9% or higher. According to the known reports, titanium dioxide which is doped, surface-treated, or coated with impurities including a metal element such as nitrogen (N), silicon (Si), aluminum (Al), or tungsten (W), or a metal compound such as aluminum oxide ($Al_2O_3$) or aluminum hydroxide ($Al(OH_3)$) is known to exhibit a superior bleaching effect, but the present invention demonstrated that the composition for bleaching tooth including rutile type titanium dioxide without impurity elements has higher photoactivity to exhibit a superior bleaching effect.

Therefore, according to the composition for bleaching tooth of the present invention, the composition satisfying the above conditions of crystallinity, particle size and purity may exhibit more excellent bleaching effect than the commercially available compositions for bleaching tooth, and also, production costs may be reduced, because additional doping or surface treatment of titanium dioxide is not needed.

The rutile type titanium dioxide may be included in an amount of about 0.01 to about 5% by weight, preferably about 0.01 to about 1% by weight, based on the total weight of the composition. When the content of titanium dioxide is within the above range, a proper bleaching effect may be obtained without side effects in human body.

The composition for bleaching tooth of the present invention includes peroxide.

The peroxide is ionized in an aqueous solution to generate free radicals, which break down stain-causing molecules on tooth. As the peroxide, any material commonly used in the art for bleaching of tooth may be used. Hydrogen peroxide, perborate, percarbonate, perphosphate, persulfate, calcium peroxide, magnesium peroxide, carbamide peroxide, etc. may be exemplified, and hydrogen peroxide may be preferably used.

The peroxide may be included in an amount of about 3 to about 45% by weight, or about 3 to about 35% by weight, or about 3 to about 15% by weight, based on the total weight of the composition. Compared to home bleaching compositions, office bleaching compositions may include a high concentration of hydrogen peroxide within the above range. When the content of the peroxide is within the above range, a proper bleaching effect may be obtained without side effects such as tooth etching.

The composition for bleaching tooth includes water, and may exist in the form of an aqueous solution including titanium dioxide and peroxide. Water may be included in a residual amount, excluding the amounts of titanium dioxide, peroxide and other additives.

According to an embodiment of the present invention, the composition for bleaching tooth of the present invention may further include an electrolyte solution.

When the electrolyte solution is included in a proper concentration and content, the bleaching effect may be further enhanced. The concentration of the electrolyte solution is preferably more than 0 mM to about 7 mM or less, or about 2 mM to about 6 mM, and its content is preferably 0.01 to 1 mg per 1 ml of the composition for bleaching tooth.

The electrolyte solution to be included may be exemplified by a phosphate buffer, a tris buffer, a tricine buffer, a MOPS buffer, etc., but is not limited thereto. Any electrolyte solution widely used in biological fields may be used without limitation.

In addition to the above components, the composition for bleaching tooth of the present invention may further include an additive such as a gelling agent, a pH adjuster, a stabilizer, a moisturizing agent, a chelating agent, a surfactant, a sweetening agent, a flavoring agent, etc., if necessary. As the additive, a material commonly used in the art to which the present invention pertains may be used in a general amount in the art, but is not particularly limited thereto.

A method of bleaching tooth using the composition for bleaching tooth of the present invention may be performed as follows.

First, the composition for bleaching tooth of the present invention is evenly applied to the surface of tooth. The application of the composition for bleaching tooth may be performed by directly applying the composition onto tooth or by applying or impregnating the composition for bleaching tooth into a substrate in advance and then attaching the substrate to teeth, but is not particularly limited thereto.

Next, the composition for bleaching tooth applied onto the surface of tooth is irradiated with light having a wavelength of about 380 to about 420 nm, preferably about 380 to about 405 nm The composition for bleaching tooth of the present invention includes rutile type titanium dioxide as described above, thereby showing photoactivity at the wavelength of visible light. Therefore, it is possible to use the composition in home bleaching, which has a difficulty in use of light in the ultraviolet wavelength range, as well as in office bleaching.

The type of a light source irradiating light within the above wavelength is not particularly limited, but exemplified by light emitting diode (LED), fluorescent light, incandescent light, etc.

Further, a light irradiation time may be determined depending on the type or intensity of the light source, discoloration degree of the target tooth and desired tooth color, and the light may be generally irradiated for about 1 to 30 minutes, preferably about 5 to 15 minutes. For more effective bleaching effect, application of the composition for bleaching tooth of the present invention may be performed once or more times within the above irradiation time. After light irradiation, the applied composition is washed by cleaning, etc.

Hereinafter, actions and effects of the present invention will be described in more detail with reference to specific Examples. However, these Examples are for illustrative purposes only, and the scope of the invention is not intended to be limited thereby.

EXAMPLE

Preparation of Titanium Dioxide-containing Colloid Solution

Preparation Example 1

5 mg of rutile type titanium dioxide powder having an average particle size of 20 nm (manufacturer: MTI Corporation) was dispersed in 50 ml of distilled water. After vigorously shaking a dispersed solution, the solution was sonicated for 20 minutes using a sonicator to prepare a colloid solution.

Immediately before light irradiation, the colloid solution was vigorously mixed again for 10 seconds.

Preparation Examples 2 to 17

Titanium dioxide-containing solutions were prepared in the same manner as in Preparation Example 1, except that titanium dioxide powders being different in phase, average particle size, manufacturer, and doping or coating shape were used. The kind of each titanium dioxide is summarized in the following Table 1.

TABLE 1

| Preparation Example | Abbreviation | Phase | Average particle size (nm) | Coating or doping | Manufacturer |
|---|---|---|---|---|---|
| 1 | TR20M | rutile | 20 | — | MTI Corporation |
| 2 | TR30U | rutile | 30 | — | US Research Nanomaterials |
| 3 | TR50U | rutile | 50 | — | US Research Nanomaterials |
| 4 | TR100U | rutile | 100 | — | US Research Nanomaterials |
| 5 | TR100S | rutile | 100 | — | Sigma-Aldrich |
| 6 | TR165U | rutile | 165 | — | US Research Nanomaterials |
| 7 | TRSi30U | rutile | 30 | coated with Silicon | US Research Nanomaterials |
| 8 | P25 | mixture | 25 | anatase:rutile = 80:20 | Evonik |
| 9 | TAW10U | anatase | 10 | doped with 5.7% W | US Research Nanomaterials |
| 10 | TA20U | anatase | 20 | — | US Research Nanomaterials |
| 11 | TA30U | anatase | 30 | — | US Research Nanomaterials |
| 12 | TUSP-S | amorphous | NA | USP grade | Sigma-Aldrich |
| 13 | TA25S | anatase | 25 | — | Sigma-Aldrich |
| 14 | TM100S | amorphous | 100 | doped with 1% Mn | Sigma-Aldrich |
| 15 | MT15T | amorphous | 15 | coated with Si, Al, Alginate | Tayca Co. LTD |
| 16 | T20S | amorphous | 21 | — | Sigma-Aldrich |
| 17 | TRAl30U | rutile | 30 | coated with Al | US Research Nanomaterials |

* Purity of titanium dioxide of Preparation Examples 1 to 6 is 99% or higher.

Preparation of Composition for Bleaching Tooth

Example 1

0.1% by weight of rutile type titanium dioxide powder (abbreviation: TR30U) used in Preparation Example 2, 10% by weight of alginate, 2% by weight of gelatin, 10% by weight of ethanol, 15% by weight of hydrogen peroxide ($H_2O_2$), 3% by weight of a pH conditioner (potassium phosphate tribasic), and 59.9% by weight of water were mixed to prepare a composition for bleaching tooth.

Examples 2 to 5

Compositions for bleaching tooth were prepared in the same manner as in Example 1, except that titanium dioxide powders of Preparation Examples 3 to 6 were used, respectively.

Comparative Examples 1 to 12

Compositions for bleaching tooth were prepared in the same manner as in Example 1, except that titanium dioxide powders of Preparation Example 1 and Preparation Examples 7 to 17 were used, respectively.

Comparative Example 13

A commercially available composition for bleaching tooth (product name: Zoom2, 15% $H_2O_2$ in Korea, Discus Dental LLC, Culver City, Calif., USA) was prepared.

Components of the compositions for bleaching tooth of Examples 1 to 5 and Comparative Examples 1 to 13 are summarized in the following Table 2.

TABLE 2

| Number | Titanium dioxide | Concentration of hydrogen peroxide |
|---|---|---|
| Example 1 | Preparation Example 2 | 15% |
| Example 2 | Preparation Example 3 | 15% |
| Example 3 | Preparation Example 4 | 15% |
| Example 4 | Preparation Example 5 | 15% |
| Example 5 | Preparation Example 6 | 15% |
| Comparative Example 1 | Preparation Example 1 | 15% |
| Comparative Example 2 | Preparation Example 7 | 15% |
| Comparative Example 3 | Preparation Example 8 | 15% |
| Comparative Example 4 | Preparation Example 9 | 15% |
| Comparative Example 5 | Preparation Example 10 | 15% |
| Comparative Example 6 | Preparation Example 11 | 15% |
| Comparative Example 7 | Preparation Example 12 | 15% |
| Comparative Example 8 | Preparation Example 13 | 15% |
| Comparative Example 9 | Preparation Example 14 | 15% |
| Comparative Example 10 | Preparation Example 15 | 15% |
| Comparative Example 11 | Preparation Example 16 | 15% |
| Comparative Example 12 | Preparation Example 17 | 15% |
| Comparative Example 13 | none | 15% |

Experimental Example

Assessment of Photoactivity

Each of the titanium dioxide colloid solutions prepared in Preparation Examples 1 to 17 was mixed with a 30% hydrogen peroxide aqueous solution and 10 ppm of methylene blue, and each mixture was injected to a 96-well plate. In this regard, titanium dioxide was prepared in a concentration of 0.05 mg/ml.

Each solution was irradiated with LED at 380 nm and 405 nm for 10 minutes, and then decomposition of methylene blue was measured. Methylene blue exhibits a maximum absorbance at 660 nm, and its decomposition may be determined by measuring changes of absorbance at this wavelength.

According to the measurement method, decompositions of methylene blue by the titanium dioxide solutions of Preparation Examples 1 to 17 and only by 30% hydrogen peroxide aqueous solution (Preparation Example 18) were measured and given in a graph of FIG. 1.

Referring to FIG. 1, non-coated or doped rutile type titanium dioxide showed higher activity than anatase type titanium dioxide (Preparation Examples 9 to 11, and Preparation Example 13), amorphous titanium dioxide (Preparation Examples 12, 14, 15 and 16), and anatase and rutile-mixed type (Preparation Example 8) in all ranges of average particle size (Preparation Examples 1 to 6), and also showed higher activity than titanium dioxide particles doped or coated with other elements in Preparation Example 7, Preparation Example 9, Preparation Example 14, Preparation Example 15, and Preparation Example 17.

Compared to Preparation Examples 1 to 6, photoactivity of rutile type titanium dioxide was generally increased in proportion to its particle size. Similar photoactivity was observed in the average particle size range of 30 nm or larger. In particular, Preparation Examples 4 and 5 having the average particle size of 100 nm, and Preparation Example 6 having the average particle size of 165 nm showed the highest photoactivity, and they also showed the activity even at the wavelength of visible light, indicating high bleaching activity. In contrast, Preparation Example 1 having the average particle size of 20 nm showed lower photoactivity than those having the average particle size of 30 nm or larger.

The composition of Preparation Example 18 containing only hydrogen peroxide without titanium dioxide showed little methylene blue decomposition activity, indirectly suggesting that the bleaching effect may be hardly obtained without the light activation.

Assessment of Tooth Bleaching Effect 20 anterior and posterior teeth were used to assess the bleaching effect. Teeth extracted for periodontal and orthodontic reasons were sterilized, and immediately frozen. For discoloration of the teeth, a mixture of green tea and coffee was put in a 50 ml conical tube, and the teeth were placed in this tube, followed by gently shaking at 30° C. for 2 weeks for discoloration.

After 2 weeks, the discolored teeth were randomly divided into 2 groups, each group containing 10 teeth. The bleaching composition of Example 3 was applied to one group, and Zoom2 of Example 13 was applied to the other group.

The compositions of Example 3 and Comparative Example 13 were applied to teeth, and then irradiated with LED at 380 nm for 15 minutes. This procedure was repeated three times.

The result of bleaching was assessed by two methods at 7 days after application. One method is a visual assessment method using a shade guide (Vitapan Classical Shade Guide, Bad Sackingen, Germany) and the other is a digital assessment method using a digital camera (Nikon D90, Nikon, Japan). For visual assessment, Vitapan Classical shade guide was arranged from B1 to C4 (B1, A1, B2, D2, A2, C1, C2, D4, A3, D3, B3, A3.5, B4, C3, A4, C4), with each shade tab given a sequential numerical ranking from 1 to 16. The visual assessment was performed based on this shade guide.

The digital assessment was performed according to a method as used by Polydorou. Images were taken in a dark room under standard lighting conditions using a ring flash (Nikon R1C1 Flash System, Nikon). Individual images were taken together with the VITA shade guide, a standard gray, and a reference tooth. These three reference colors were used to correct lighting and color. In this regard, to obtain images of the same size, a stationary tripod was used.

For digital assessment, two images were taken under the same lighting conditions at 7 days before and after application of the bleaching composition, and two images were overlapped using a photoshop layer tool. 16 areas were randomly selected using a polygonal lasso tool. $L^*$, $a^*$, and $b^*$ values were measured using a color selection tool at the point of the polygonal lasso. $L^*$, $a^*$, and $b^*$ values were measured with respect to 16 areas at the same position of the images. A color difference between before and after application of the composition for bleaching tooth was calculated, and this difference was represented by $\Delta L^*$, $\Delta a^*$, and $\Delta b^*$.

This color difference ($\Delta E^*$) was calculated by the following Equation.

$$\Delta E^* = \{(\Delta L^*)^2 + (\Delta a^*)^2 + (\Delta b^*)^2\}^{1/2}$$

The t-test was used in statistical analysis (a significance level of 0.05).

Color changes in the visual assessment and digital assessment of Example 3 and Comparative Example 13 are given in the following Table 3.

TABLE 3

| Assessment item | Mean ± Standard Deviation | | p value |
| --- | --- | --- | --- |
| | Example 3 | Comparative Example 13 | |
| Visual assessment | VC 8.90 ± 2.56 | VC 6.80 ± 2.10 | 0.0600 |
| Digital assessment | $\Delta E^*$ 8.75 ± 1.56 | $\Delta E^*$ 6.44 ± 1.31 | 0.0021 |
| | $\Delta L^*$ 5.73 ± 1.12 | $\Delta L^*$ 3.83 ± 0.75 | |
| | $\Delta a^*$ −0.44 ± 0.40 | $\Delta a^*$ −0.59 ± 0.55 | |
| | $\Delta b^*$ −6.28 ± 1.49 | $\Delta b^*$ −4.74 ± 1.52 | |

Referring to Table 3, Example 3 showed a similar result in the visual assessment and a better result in the digital assessment, compared to that of Comparative Example 13.

Images of the teeth before and after application of the bleaching compositions of Example 3 and Comparative Example 13 are given in FIG. 2.

In FIG. 2, (a) and (b) represent images before and after application of the bleaching composition of Example 3, respectively and (c) and (d) represent images before and after application of the bleaching composition of Comparative Example 3, respectively.

Referring to FIG. 2, (a) and (b) showed that Example 3 exhibited a color difference of 11 grades in the visual assessment and a color difference of 10.47 in the digital assessment, whereas (c) and (d) showed that Example 13 exhibited a color difference of 10 grades in the visual assessment and a color difference of 7.31 in the digital assessment.

What is claimed is:

1. A composition for bleaching tooth, comprising rutile titanium dioxide ($TiO_2$) having an average particle size of 50 to 180 nm and a purity of 97% or higher, peroxide, and water.

2. The composition of claim 1, wherein the titanium dioxide is included in an amount of 0.01 to 5% by weight, based on the total weight of the composition.

3. The composition of claim 1, wherein the peroxide is one or more selected from the group consisting of hydrogen peroxide, perborate, percarbonate, perphosphate, persulfate, calcium peroxide, magnesium peroxide, and carbamide peroxide.

4. The composition of claim 1, wherein the peroxide is included in an amount of 3 to 45% by weight, based on the total weight of the composition.

* * * * *